United States Patent [19]

Gordon et al.

[11] Patent Number: 4,891,213

[45] Date of Patent: Jan. 2, 1990

[54] NAIL ENAMEL CONTAINING MICROCRYSTALLINE CELLULOSE

[75] Inventors: Harry W. Gordon, Wantagh; Kenneth Chung, Greenlawn, both of N.Y.

[73] Assignee: Del Laboratories, Inc., Farmingdale, N.Y.

[21] Appl. No.: 863,927

[22] Filed: May 15, 1986

Related U.S. Application Data

[63] Continuation of Ser. No. 658,420, Oct. 5, 1984, abandoned.

[51] Int. Cl.⁴ .............................................. A61K 7/043
[52] U.S. Cl. ..................................................... 424/61
[58] Field of Search ........................................... 424/61

[56] References Cited

U.S. PATENT DOCUMENTS

| | | | |
|---|---|---|---|
| 3,146,170 | 8/1964 | Battista | 424/61 X |
| 3,301,760 | 1/1967 | Jewel | 424/61 |
| 3,342,686 | 9/1967 | Jewel | 424/61 |
| 4,137,302 | 1/1979 | Humbert et al. | 424/61 X |
| 4,179,304 | 12/1979 | Rossomando | 424/61 X |
| 4,374,702 | 2/1983 | Turbak et al. | 162/100 |
| 4,483,743 | 11/1984 | Turbak et al. | 162/100 |

*Primary Examiner*—John W. Rollins
*Assistant Examiner*—W. Catchpole
*Attorney, Agent, or Firm*—Kirschstein, Ottinger, Israel & Schiefmiller

[57] ABSTRACT

Nail enamel compositions, particularly of the nitrocellulose type, have added a small amount of microcrystalline cellulose powder. When the compositions are applied to the nails, the microcrystalline cellulose particles act in lieu of long thin fibers to reinforce and strengthen the enamel coating while some of the particles tend to settle into the valleys between the nail ridges to smooth out the surface of the nails. These enamel compositions can be used without prior application of a filler coat to give a smooth, glossy, reinforced finish to the nails with no fibers visible.

2 Claims, 3 Drawing Sheets

FIG. I

NAIL ENAMEL CONTAINING MICROCRYSTALLINE CELLULOSE

This is a continuaton of application Ser. No. 658,420, filed Oct. 5, 1984, now abandoned.

BACKGROUND OF INVENTION

1. Field of Invention

The present invention relates to nail enamel compositions and compositions for filling in imperfections on the broad surface of human nails.

2. Description of the Prior Art

It has long been recognized that when nail enamel or polish is applied to a human nail and dries, the appearance of the enamel or polish coating may be marred by cracking, peeling or chipping and by the natural ridges, bumps or other imperfections in the nail which are highlighted by the polish and give the finish an uneven appearance.

To help ameliorate the cracking, peeling and chipping problems, nail enamel formulations have been made incorporating strengthening fibers of synthetic materials, such as nylon fibers, which form a grid or mesh through the dried nail enamel coating and help prevent degradation or chipping of the coating.

In order to help disguise the natural ridges, bumps and other imperfections in the nail, it has been the conventional practice in the nail-care industry to provide a filling composition, usually containing an impalpable powder such as talc as a filling ingredient. Such filling compositions usually are applied to the nail prior to the application of a polish, i.e. enamel coat (or sometimes after application of an enamel coat) and tend to smooth out, i.e. level, the appearance of the nail, with the talc settling into the depressions so that a fairly even substrate is provided for the subsequent application of a nail polish coating.

The use of the conventional talc-containing filling compositions in association with fiber-containing nail enamels suffers from a significant number of drawbacks. In the first place, the user must generally apply one or two coats of filler and allow each coat to dry, and then apply one or two coats of nail enamel. Some users apply one or two coats of enamel before application of the filling ingredient and apply enamel again after the filler. This process, including drying time, is painstaking and time-consuming (often taking an hour or more). Furthermore, the talc in the filler often detracts from the gloss of the enamel overcoat.

A further drawback exists with respect to conventional fiber-containing enamels themselves. Upon drying, the enamel coating frequently shows the fibers on the nail, marring the nail appearance.

Although it has long been recognized in the cosmetics trade that it would be desirable to be able to apply a fibercontaining enamel to the nails without previously applying a filling base composition, experience has shown that the nylon or similar straight fibers contained in conventional enamel compositions do not fill in the valleys between nail ridges and so such an enamel finish prominently shows the ridges and valleys in the nail, which detract from the smoothness and attractiveness of the finish. To the present date, no nail enamel formulation has been created which provides a fiber-reinforced, lustrous finish with high gloss, while simultaneously filling in the valleys between the nail ridges without the need for prior application of a filling composition, and without having the fibers in the enamel show up on the nail after drying.

SUMMARY OF THE INVENTION

1. Objects of the Invention

It is an object of the present invention to provide nail enamel compositions which obviate the need for the prior application of a filling base coat.

An additional object of the present invention is to provide compositions as described above which give a lustrous, smooth high-gloss finish to the nails.

A further object of the present invention is to provide compositions as described above which contain fibers that reinforce and strengthen the nail enamel coating to help prevent cracking, chipping, peeling and the like.

Still another object of the present invention is to provide compositions as described above wherein the reinforcing fibers also act as filling material.

Yet another object of the invention is to provide compositions as described above wherein the fibers in the enamel are invisible on the nail to the unassisted human eye after the enamel coating has dried.

Yet a further object of the present invention is to provide a nail enamel composition which can be used to apply a lustrous, high-gloss, ridge-free finish to the nails in substantially less time and with substantially less effort than was the case with previously known nail enamels and polishes.

2. Brief Description of the Invention

In keeping with these objects and others which will become apparent hereinafter, the present invention resides, briefly stated, in nitrocellulose-type nail enamel compositions which include a small percentage of fibrous microcrystalline cellulose material. The concentration of the microcrystalline cellulose in the compositions can vary widely but has been found to have an optimum range of between about 0.1 to about 3.0% by weight of the liquid nail enamel.

The special microcrystalline cellulose is available in a variety of forms, and the one which has been found to be particularly useful in connection with the present invention is the "AVICEL" line of cellulose products sold by FMC Corporation (Philadelphia, Pa.), which has been used as a natural additive to a number of cosmetic products as a stabilizer, a colloidal suspension agent and an emulsifier or emulsion stabilizer. It has now been discovered that certain microcrystalline cellulose products are uniquely well-suited for use in binding and reinforcing a nail enamel composition and in forming an intermeshed protective grid over the nail, while at the same time some of the short, irregular cellulose "shavings" or "flakes" tend to be deposited into the filled nail ridges to create a smooth finish without detracting from nail enamel gloss, as does talc.

It has also been found that certain microcrystalline cellulose products are naturally compatible with nitrocellulose-containing nail enamels, of the type that are commercially available, and can be added to and dispersed through such compositions with a minimum of effort to create greatly improved nail enamel products.

DETAILED DESCRIPTION OF THE INVENTION

Figure 1:
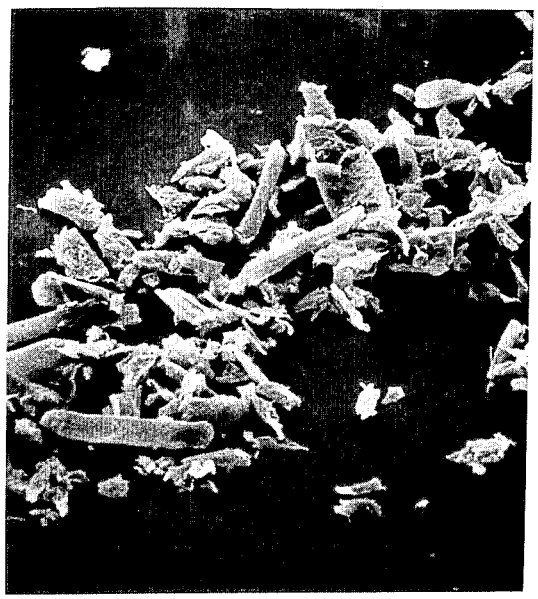
FIG. 1 is a photograph of a powder droplet of "AVICEL PH 105" microcrystalline cellulose magnified 300 times.

Typical conventional nail polish compositions of the nitrocellulose type include (a) a solvent system, generally including volatile organic solvents such as ethyl acetate, butyl acetate, isopropyl alcohol, butyl alcohol or toluene, or a mixture of some or all of these solvents; (b) a plasticizer such as camphor or dibutyl phthalate; (c) a nitrocellulose film former; and, frequently, (d) a hardener such as toluene-sulfonamide/formaldehyde resin. There may also be coloring agents (such as a variety of dyes approved for cosmetic use), acrylate polymers and ultraviolet absorbing agents, among numerous other possible additives.

With respect to the proportions of the above ingredients in a conventional enamel composition, typical ranges for percentages by weight of the various components would be about 60 to about 80% solvent system, about 5 to about 20% hardener, about 2 to about 15% nitrocellulose, about 0.5 to about 8.0% plasticizer and about 0.1 to about 5.0% coloring agents and other additives.

In fiber-containing compositions, a generally small amount (about 0.1 to about 2.0% by weight) of synthetic fibrous material, such as nylon fibers, is added to and dispersed in the solvent system. The fibers provide a reinforcing, binding and strengthening function for the dried nail enamel coating. However, conventionally used synthetic fibers such as nylon have long, straight, thin, filament-like structures and tend to lie across and follow the nail ridges when applied to the nail rather than filling in between such ridges. For example, the nail polish compositions disclosed in U.S. Pat. Nos. 3,301,760 and 3,342,686 include nylon fibers approximately ⅛ inch (3.15 mm) in length and 0.1 mm in diameter. Thus, if no prior application of a filling base coat is made, a conventional fiber-containing nail enamel will dry with the nail ridges and valleys prominently in evidence. If the enamel is colored, the enamel coat may even highlight the nail ridges and accentuate or exaggerate their appearance when no filler is applied.

Furthermore, the nylon fibers tend to be visible on the nail in the dried enamel coating.

As noted previously, the conventional practice has been to apply one or two coats of talc-containing filler to the nail (sometimes after prior application of an enamel base coat), allowing each coat to dry, and then to apply a fiber-containing enamel. This time-consuming and painstaking procedure often does not yield a high gloss coating because the talc in the filler detracts from the luster and gloss of the enamel coating.

The liquid nail enamel compositions of the present invention, on the other hand, include about 0.1 to 3.0% by weight of microcrystalline cellulose, such as one of the "AVICEL" products sold by FMC Corporation. Of particular value is a hydrolyzed and spray-dried alpha-cellulose product marketed by FMC Corporation under the trade designation "AVICEL PH 105".

Microcrystalline cellulose products are generally cellulose derivatives substituted by ethyl, methyl, hydroxypropyl and other ionic or non-ionic groups. These versatile polymers are useful as suspending agents, emulsin stabilizers and protective colloids. The cosmetic-grade "AVICEL" microcrystalline cellulose products are available in the form of fine white crystalline powders which are easily handled and which are conveniently dispersible in nail enamel solvent systems.

"AVICEL PH 105", which is the microcrystalline cellulose of choice in connection with the present invention, takes the physical form of very fine irregular "shavings" or "flakes", generally on the order of no more than 50 microns (0.05 mm) in their maximum dimension.

Figure 2:
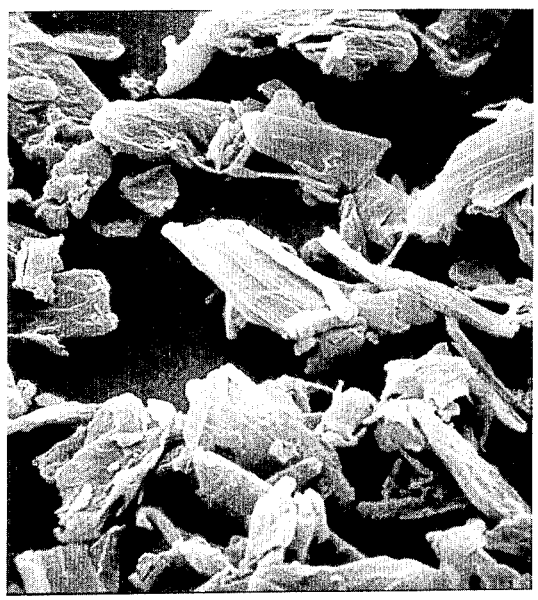
FIG. 2 is a photograph of a powder droplet of "AVICEL PH 105" magnified 1,000 times.
Figure 3:
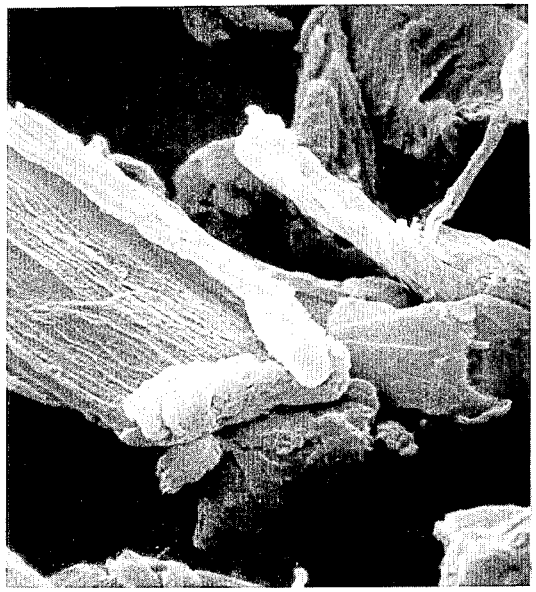
FIG. 3 is a photograph of a powder droplet of "AVICEL PH 105" magnified 3,000 times.

FIGS. 1 through 3 are photographs taken through an electron microscope showing the configuration and appearance of the "AVICEL PH 105" particles under different degrees of magnification (300 times to 3,000 times, respectively). As may be seen from the photographs, the microcrystalline cellulose particles are composites of fibrous structures but are in the form of shavings with rough surfaces and jagged edges. Furthermore, the particles tend to have curled ends which are adapted for forming an intermeshed grid in a film matrix, such as within a nitrocellulose nail enamel film.

The "AVICEL" or other microcrystalline cellulose material is added, according to the present invention, to a conventional nail enamel solvent system and dispersed therethrough, such as by rapid stirring or agitation. Subsequently, the other nail enamel components, such as the plasticizers, nitrocellulose film former, hardeners, coloring agents, and the like, are added in conventional fashion and the completed nail enamel product is produced by known means. Alternatively, the microcrystalline cellulose can be added to the nail enamel formulation after the plasticizers, hardeners, and other components have been mixed with the solvent system.

The products of the subject invention, created by the addition of microcrystalline cellulose powder to otherwise conventional nitrocellulose nail enamel compositions, have a number of unique advantages in comparison with nail enamels previously known in the art. Preferred microcrystalline cellulose materials for use in the present compositions consist of particles having a configuration substantially as shown in FIGS. 1-3. Because the microcrystalline cellulose material remains well dispersed and colloidally suspended in the nail enamel liquid, and because of the physical configuration of the cellulose particles (as shown in FIGS. 1-3), they act in lieu of conventional long synthetic fibers, such as nylon fibers, to reinforce and strengthen the enamel coating to help prevent peeling, cracking and chipping. The microcrystalline cellulose particles tend to become dispersed throughout the enamel film applied to the nail in an intermeshed grid embedded in the enamel, forming a protective overcoat on the nail.

Furthermore, many of the microcrystalline cellulose particles in an applied coat of the instant nail enamels tend to settle into the ridges in the nail and remain there after evaporation of the solvent, thus acting as fillers to smooth and even out the nail surface—yet, unlike talc, the cellulose material has been found not to detract from the gloss or luster of the nail enamel finish. In addition, whereas with conventional fiber-containing enamels the fibers may be visible on the nail once the solvent has evaporated, which detracts from the beauty and smoothness of the enamel finish, microcrystalline cellulose fibers, by virtue of their short length and microscopic size, are substantially invisible in the dried enamel coating and do not protrude noticeably above the smooth surface of the dried coating.

Thus, the nail enamel compositions of the present invention, which incorporate small quantities of microcrystalline cellulose, act as combination fillers and reinforcing nail enamel products. Instead of having to apply at least two coats of ridge filler and then two coats of fiber-containing enamel to the nail, a consumer using the novel compositions of the invention can achieve with only one or two coats a finish which has higher gloss (because of the absence of talc) and is smoother (because of the use of short, irregular, microscopic shavings instead of fibers) than is achieved by the use of conventional filling and nail enamel products in combination. Moreover, the time for completion of the entire nail beautification process can be reduced with the compositions of the present invention from one hour or more to approximately 15 minutes, with better results being achieved in terms of nail appearance.

The following is an illustrative example of the preparation of a nail enamel composition in accordance with the present invention. This example is not intended, however, to limit or restrict the scope of the invention in any way and should not be construed as identifying specific materials, parameters or ranges which must be utilized exclusively in order to make or use the compositions of the present invention.

EXAMPLE

A red nail enamel composition according to the present invention was made by conventional means using the following ingredients:

| Ingredients | Percentage by Weight |
|---|---|
| Butyl acetate | 30.00 |
| Toluene | 25.00 |
| Nitrocellulose | 15.00 |
| Ethyl acetate | 8.00 |
| Toluenesulfonamide/formaldehyde resin | 7.00 |
| Isopropyl alcohol | 6.00 |
| Dibutyl phthalate | 5.00 |
| Camphor | 1.20 |
| Stearalkonium hectorite | 0.80 |
| "AVICEL PH 105" microcrystalline cellulose | 0.50 |
| D & C Red No. 34 Calcium Lake | 0.50 |
| Other additives (e.g., bismuth oxychloride and acrylates copolymer) | 1.00 |

The microcrytstalline cellulose component was added to the solvent system (consisting of butyl acetate, toluene acetate and isopropyl alcohol) and thoroughly dispersed therein by agitation and stirring. After mixing all of the above ingredients according to conventional methods, a smooth flowing liquid red enamel was produced. When applied to users' nails, the enamel was found to produce a substantially ridge-free, lustrous, high-gloss finish with no fibers visible on the nails.

The nail enamel compositions of the invention are utilized in conventional manner by application of a thin coating to the nails. If desired, a primer coat of some other nail-care composition can be applied first, but there is no need for the prior application of any filling composition. Multiple coats of the enamels of the present invention can be applied to the nails for additional gloss and protection, with each coat being allowed to thoroughly dry before the next coat is applied.

Aside from the enormous advantages of the subject compositions which were set forth previously, namely, the fact that they enable the use of one product to give a high gloss, ridge-free, fiber-reinforced finish and the fact that the finish shows no visible fibers on the nail, these compositions are easy and inexpensive to formulate. Only a small quantity of micrycrystalline cellulose is required to achieve the advantages of the invention and this cellulose material may be simply combined with conventional nail enamel bases using existing production equipment.

It will thus be seen that there are provided compositions which achieve the various objects of the invention and which are well adapted to meet the conditions of practical use. As various possible embodiments might be made of the above invention and as various changes might be made in the embodiments set forth, it is to be understood that all matter herein described is to be interpreted as illustrative and not in a limiting sense.

What is claimed as new and desired to be protected by Letters Patent is set forth in the appended claims.

1. A non-aqueous liquid nail polish composition for one-time application on a human nail to provide, upon drying, a smooth, ridge-free, lustrous, high-gloss, dried coating resistant to water removal, said non-aqueous composition comprising:

a solvent in the range of about 60% to about 80% by weight of the composition;

a hardener in the range of about 5% to about 20% by weight of the composition;

a film former in the range of about 2% to about 15% by weight of the composition;

a plasticizer in the range of about 0.5% to about 8% by weight of the composition;

a coloring agent in the range of about 0.1% to about 5% by weight of the composition; and hydrolyzed, alpha-cellulose, microcrystalline cellulose powder in the range of about 0.1% to about 3% by weight of the composition, said cellulose powder being constituted of particles on the order of no more than 50 microns in their maximum dimension, said particles being dispersed and colloidally suspended in the non-aqueous liquid composition, said particles forming an intermeshed grid embedded within said dried coating to resist removal by water as well as peeling, cracking and chipping of said dried coating.

2. The non-aqueous composition as recited in claim 1, comprising by weight of the non-aqueous composition about 30% butyl acetate, 25% toluene, 15% nitrocellulose, 8% ethyl acetate, 7% toluenesulfonamide/formaldehyde resin, 6% isopropyl alcohol, 5% dibutyl phthalate, 1.2% camphor, 0.8% stearalkonium hectorite and 0.5% cellulose powder.

* * * * *